US00RE39562E

(19) United States
(12) Reissued Patent
Rao et al.

(10) Patent Number: US RE39,562 E
(45) Date of Reissued Patent: Apr. 10, 2007

(54) HIGH LYSINE DERIVATIVES OF α-HORDOTHIONIN

(75) Inventors: A. Gururaj Rao, Urbandale, IA (US); Larry R. Beach, Des Moines, IA (US)

(73) Assignee: Pioneer Hi-Bred International, Inc., Johnston, IA (US)

(21) Appl. No.: 10/010,709

(22) Filed: Nov. 5, 2001

Related U.S. Patent Documents

Reissue of:
(64) Patent No.: 5,990,389
Issued: Nov. 23, 1999
Appl. No.: 08/838,763
Filed: Apr. 10, 1997

U.S. Applications:
(63) Continuation of application No. 08/575,654, filed on Dec. 20, 1995, now abandoned, which is a continuation of application No. 08/369,975, filed on Jan. 6, 1995, now abandoned, which is a continuation of application No. 08/003,885, filed on Jan. 13, 1993, now abandoned.

(51) Int. Cl.
*A01H 5/00* (2006.01)
*C12N 15/82* (2006.01)
*C12N 15/29* (2006.01)
*C07K 4/415* (2006.01)

(52) U.S. Cl. ..... 800/301; 800/279; 514/2; 435/418; 435/252.3; 435/320.1; 530/370; 536/23.6

(58) Field of Classification Search ..... 800/301, 800/279; 530/300; 435/419, 412, 320.1, 252.3, 435/70.1; 514/2; 536/23.6
See application file for complete search history.

(56) References Cited

U.S. PATENT DOCUMENTS 5,703,049 A * 12/1997 Rao ..... 514/12

FOREIGN PATENT DOCUMENTS

| | | | |
|---|---|---|---|
| EP | 0 318 341 | A1 * | 5/1989 |
| EP | 0 502 718 | A1 * | 9/1992 |
| WO | WO 89/04371 | A1 * | 5/1989 |
| WO | WO 92/14822 | A1 * | 9/1992 |
| WO | WO 93/03160 | A1 * | 2/1993 |
| WO | WO 93/19190 | A1 * | 9/1993 |
| WO | WO 94/10315 | A2 * | 5/1994 |
| WO | WO 94/16078 | A2 * | 7/1994 |
| WO | WO 94/20628 | A2 * | 9/1994 |

OTHER PUBLICATIONS

Altenbach et al., Manipulation of methionine–rich protein genes in plant seeds, Trends in Biotechnology (1990) 8(6):156–160.

Altenbach et al., Accumulation of a Brazil nut albumin in seed of transgenic canola results in enhanced levels of seed protein methionine, Plant Molecular Biology (1992) 18:235–245.

Anderson et al., A Transgenic Corn Line with Altered Levels of a High–Methionine Storage Protein, J Cell Biochem Suppl (1992) 16F:225 abstract Y304.

Beach et al., Enhancing the Nutritional Value of Seed Crops, Curr Top Plant Physiol: Biosynthesis and Molecular Regulation of Amino Acids in Plants (1992) 7:229–238.

Florack et al., Expression of biologically active hordothionins in tobacco. Effects of pre–and pro–sequences at the amino and carboxyl termini of the hordothionin precursor on mature protein expression and sorting, Plant Molecular Biology (1994) 24:83–96.

Garcia–Olmeda et al., Trypsin/alpha–amylase inhibitors and thionins from cereals: possible role in crop protection, Journal of Exp. Botany Supplemental (1991) 42(238):4 and abstract P1.5.

Karchi et al., Seed–specific expression of a bacterial desensitized aspartate kinase increase the production of seed threonine and methionine in transgenic tobacco, The Plant Journal (1993) 3(5):721–727.

Karchi et al., Lysine synthesis and catabolism are coordinately regulated during tobacco seed development, Proc. Natl. Acad. Sci. USA (1994) 91:2577–2581.

Maddox et al., Cloning of a barley gene alpha–hordothionin, and expression in transgenic tobacco, Journal of Cellular Biochemistry (1992) Supplement 16F, p. 217 and abstract Y212.

Rao et al., Validation of the Structure–Function Properties of Apha–Hordothionin and Derivatives Through Protein Modeling, Abstract—Advances in Gene Technology: Protein Enginering and Beyond, Miami Bio/Technology Winter Symposium (1993) vol. 3, p. 117.

Rao et al., Structure–function validation of high lysine analogs of alpha–hordothionin designed by protein modeling, Protein Engineering (1994) 7(12):1485–1493.

Florack et al., Synthetic hordothionin genes as tools for bacterial disease resistance breeding, Agricultural Biotechnology in Focus in the Netherlands (1990) pp. 39–48, Dekkers et al., eds, Pudoc, the Netherlands.

Krebbers et al., Expression of Modified Seed Storage Proteins in Transgenic Plants, Transgenic Plants (1992) pp. 37–60, Hiatt, ed., Marcel Dekker, Inc. New York.

Ponz et al., Cloning and nucleotide sequence of a cDNA encoding the precursor of the barley toxin–hordothionin, Eur. J. Biochem. (1986) 156:131–135.

Altenbach S.B. et al., "Manipulation of Methionine–Rich Protein Genes in Plant Seeds", *Trends in Biotechnology,* vol. 8, No. 6, 1990 pp. 156–160.*

(Continued)

*Primary Examiner*—Anne Kubelik
(74) *Attorney, Agent, or Firm*—Kathryn K. Lappegard; Pioneer Hi-Bred International, Inc.

(57) ABSTRACT

Derivatives of α-hordothionin made by position-specific substitution with lysine residues provide lysine enrichment while retaining the antifungal activity of the parent compound.

21 Claims, 4 Drawing Sheets

OTHER PUBLICATIONS

Altenbach S.B. et al., "Accummulation of a Braxil Nut Albumin in Seed of Transgenic Canola Results in Enhanced Levels of Seed Protein Methionine", *Plant Molecular Biology,* 18: 235–245, 1992 pp. 235–245.*

Anderson J. et al., "A Transgenic Corn Line with Altered Levels of a High–Methionine Storage Protein", *J. Cell Biochem Suppl.,* vol. 16F. p. 225, 1992, abstract.*

Beach, L.R. et al., "Enchancing the nutritional value of Seed Crops", *Current Top, Plant Physiol.: Biosynthesis & Molecular Regulation of Amino Acids in Plants,* vol. 7, 1992 pp. 229–238.*

Florack, D.E.A. et al. "Expression of biologically active hordothionin in tobacco. Effects of pre–and pro–sequences at the amino and carboxyl termini of the hordothionin precursor on mature protein expression and sorting". *Plant Molecular Biology* vol. 24 1994, pp. 83–96.*

Garcia–Olmeda, F. et al. "Trypsin/alpha–amylase inhibitors and thionins from cereals: possible role in crop protection", *Journal of Exp. Botany Supplement,* vol. 42. No. 238, May 1991 p. 4 and abstract p. 1.5.*

Karachi H. et al., "Seed Specific Expression of a Bacterial Desensitized Aspartate Kinase Increases the Production of Seed Threonine and Methionine in Transgenic Tobacco", *The Plant Journal,* vol, 3 No. 5 pp. 721–727, 1993.*

Karachi H. et al., "Lysine synthesis and catabolism are coordinately regulated during tobacco seed development" PNAS 91, 1994 pp. 2577–2581. p. 2581 left column, last line right column.*

Maddox, J. et al., "Cloning of a barley gene alpha–hordothionin, and expression in transgenic tobacco" *J. Cell Biochem. Suppl.* vol. 16F 1992 p. 217 and abstract p.212.*

Rao A.G. et al., "Validation of the Structure–function properties of alpha–hordothionin and derivatives through protein modeling"–see abstract; *Protein Engineering: Supplement, Advances in Gene Technology* Protein Engineering and Beyond. Miami Winter symposium, Jam. 17–22, 1993 vol. 6, 1993.*

Rao A.G. et al., "Structure–Function Validation of High Lysine Analogs of α–Hordothionin Designed by Protein Modeling", *Protein Engineering,* vol. 7, No. 12, pp. 1485–1493, Dec. 1994.*

Florack et al. Synthetic hordothionin genes as tools for bacterial disease resostance breeding. In: Agricultural Biotechnology in Focus in the Netherlands. Dekkers et al. eds. Pudoc. The Netherlands. pp. 39–48, 1990.*

Krebbers et al. Expression of modified Seed storage proteins in transgenic plants. In:Transgenic Plants. Hiatt. ed. Marcel Dekker, Inc., New York, pp. 37–60. 1992.*

Ponz et al. Cloning and nucleotide sequence of a cDNA encoding the precursor of the barley toxin –hordothionin. Eur. J. Biochem. vol., 156. pp. 131–135, 1986.*

* cited by examiner

AMENDED

HIGH LYSINE DERIVATIVES OF α-HORDOTHIONIN

Matter enclosed in heavy brackets [ ] appears in the original patent but forms no part of this reissue specification; matter printed in italics indicates the additions made by reissue.

CROSS-REFERENCE TO RELATED APPLICATIONS

This application is a *reissue of U.S. Pat. No. 5,990,389, which is a* continuation of application Ser. No. 08/575,654, filed Dec. 20, 1995, now abandoned, which was a continuation of application Ser. No. 08/369,975, filed Jan. 6, 1995, now abandoned, which was a continuation of application Ser. No. 08/003,885, filed Jan. 13, 1993, now abandoned.

TECHNICAL FIELD

This invention relates to derivatives of α-hordothionin which provide higher percentages of lysine while retaining the antifungal functionality of hordothionins.

BACKGROUND OF THE INVENTION

Disease resistance is an important objective of the genetic engineering of crop plants. Numerous fungi and bacteria are serious pests of common agricultural crops. One method of controlling diseases has been to apply antimicrobial organic or semiorganic chemicals to crops. This method has numerous, art-recognized problems. A more recent method of control of microorganism pests has been the use of biological control organisms which are typically natural competitors or inhibitors of the troublesome microorganisms. However, it is difficult to apply biological control organisms to large areas, and even more difficult to cause those living organisms to remain in the treated area for an extended period. Still more recently, techniques in recombinant DNA have provided the opportunity to insert into plant cells cloned genes which express antimicrobial compounds. This technology has given rise to additional concerns about eventual microbial resistance to well-known, naturally occurring antimicrobials, particularly in the face of heavy selection pressure, which may occur in some areas. Thus, a continuing effort is underway to express naturally occurring antimicrobial compounds in plant cells directly by translation of single structural gene.

However, the use of such techniques gives rise to further problems. Crop plants are sources of sugars, starches, proteins, oils, fibers, and other raw materials. Genetic engineers would also like to modify, and often to enhance, the production of those natural plant products. Unfortunately, plant cells can only produce large quantities of a few cellular components at a time. If they are producing high levels of storage proteins, it is difficult for them to also produce high levels of antifungal compounds. Thus, genetic engineers face a quandary in designing advanced plant systems with existing molecules for protein quality enhancement and disease resistance which require concurrent high-level expression of multiple genes.

BRIEF DESCRIPTION OF THE DRAWING FIGURES

DISCLOSURE OF THE INVENTION

Figure 1:
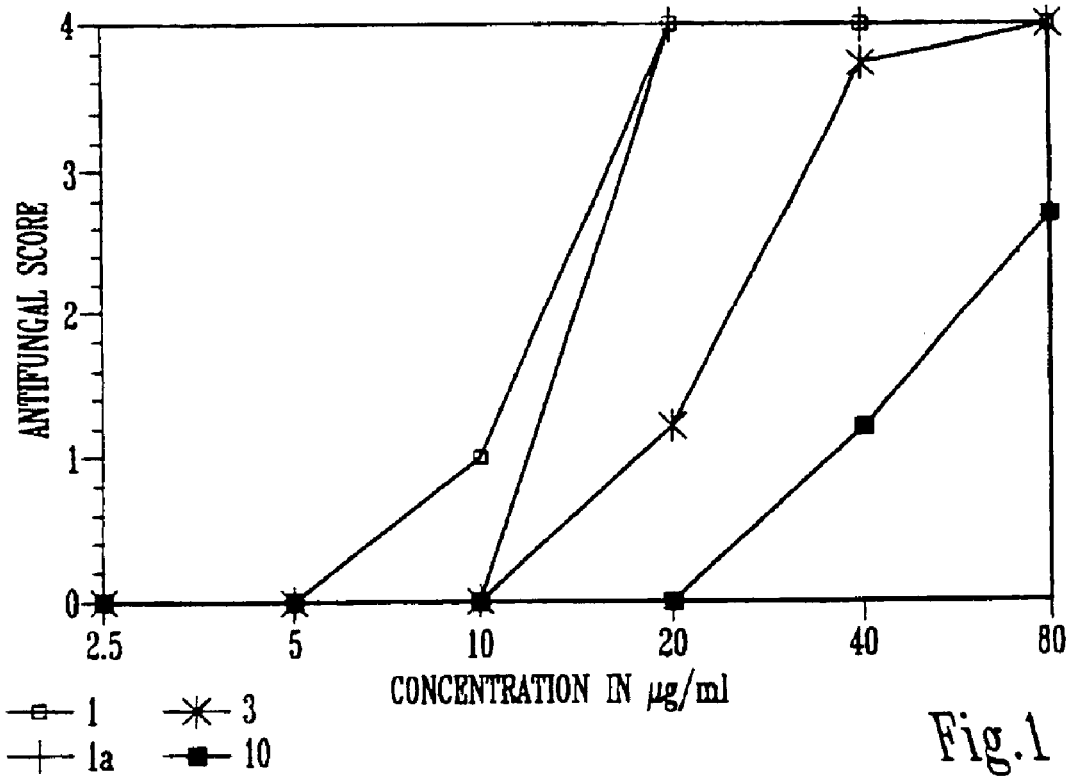
FIG. 1 is a graph of antimicrobial performance of various compounds discussed herein against S. sclerotiorum.

It has now been determined that one class of compounds, the α-hordothionins, can be modified to enhance their content of lysine while maintaining their antifungal activity. These hordothionin derivatives can be expressed to simultaneously enhance both resistance to fungal diseases and lysine content of the plant.

α-hordothionin is a 45-amino acid protein which has been well characterized. It can be isolated from seeds of barley (Hordeum vulgare) and even in its native form is especially rich in arginine and lysine residues, containing 5 residues (10) of each. The amino acid sequence is as provided in SEQUENCE I.D. No. 1. It has powerful antifungal properties. Initial work to enhance the lysine content of this protein provided a high lysine derivative *as indicated in SEQUENCE I.D. No. 2.* However, it was impossible to predict the ultimate effect of this seemingly trivial substitution on the tertiary structure and folding of the protein, and subsequent bioassays determined that this derivative did not fold to a biologically active species in vitro. In addition, both tertiary structure and folding are critical to the stability and adequate expression of the protein in vivo, and both were absent in this compound. Therefore, further analysis and functional modeling of the wild-type compound was undertaken to determine whether substitutions could be made without disrupting biological activity. Although the crystal structure of crambin, a small protein of similar size and structure, has been reported, such crystal structures have not previously been available for hordothionin or even related compounds such as purothionin and viscotoxin. We undertook to develop such structural information.

Three-dimensional modeling of the protein led us to believe that the arginine residue at position 10 was critical to retention of the appropriate 3-dimensional structure and possible folding through hydrogen bond interactions with the C-terminal residue of the protein. A lysine substitution at that point with its shorter side chains could not hydrogen bond at the same time to both the serine residue at the 2 position and to the C-terminus while maintaining the backbone structure which we had predicted. The synthetic peptide having this substitution could not be made to fold correctly, which supported this analysis. Conservation of the arginine residue at position 10 provided a protein which folded correctly, *had the sequence indicated in SEQUENCE I.D. No. 3,* and exhibited antifungal activity in a bioassay. Comparison of the structure of hordothionin with that of the loosely related (48% homologous, 30% identical) protein crambin showed that thionin had a disulfide bond linking the cysteines at positions 12 and 29 which was not bridging the corresponding positions in crambin. Accordingly, replacement of the cysteine at position 12 of thionin with lysine and replacement of the cysteine at position 29 with threonine *to produce a protein having the sequence indicated in SEQUENCE I.D. No. 4* was found not to disrupt the 3-dimensional structure of the protein, as evidenced by an energy content which was determined to be indistinguishable from that of the native protein.

Further analysis of substitutions which would not alter the 3-dimensional structure of the molecule led to replacement of Asparagine-11, Gluatamine-22 and Threonine-41 with lysine residues with virtually no steric hindrance. The resulting compound *had the sequence indicated in SEQUENCE I.D. No. 5,* containing 29% lysine residues. In addition, it was determined that by replacement of the serine residue at position 2 with aspartic acid, the arginine at position 10 could be replaced with lysine while permitting the needed hydrogen bonding with the C-terminus, *providing a compound of the sequence indicated in SEQUENCE I.D. No. 6.* It should be appreciated that these substitutions would be effective and acceptable could not have been predicted by examination of the linear sequence of the native thionin protein.

Other combinations of these substitutions were also made, *providing proteins having the sequences indicated in SEQUENCE ID No. 7 and SEQUENCE ID No. 8.* Accordingly, this invention provides proteins having the sequence of SEQUENCE I.D. No. 9 wherein the amino acid residues at one or more of positions 5, 10, 11, 12, 17, 19, 22, 30 and 41 are lysine, and the remainder of the residues at those positions are the residues at the corresponding positions in SEQUENCE ID NO: 1, *provided that the residue at position 30 is threonine when the residue at position 12 is lysine and cysteine otherwise, and the residue at position 2 is aspartic acid when the residue at position 10 is lysine and serine otherwise.* Although the native hordothionin is relatively lysine rich, a storage protein with 10% lysine residues (by number) cannot be expressed at high enough levels to obtain total protein lysine contents which are sufficient to obviate the need for lysine supplementation in poultry and swine feeds. These compounds are significantly more lysine enriched, and can be made to contain nearly thirty percent lysine residues. Without such enhanced lysine contents, it is impossible to eliminate the need for lysine supplementation of feeds. This invention thus also provides an important method for enhancing the lysine content of a plant cell or a plant, comprising the step of causing one or more proteins according to this invention to be expressed in the cell or plant.

Synthesis of the compounds was performed according to methods of peptide synthesis which are well known in the art and thus constitute no part of this invention. In vitro, we have synthesized the compounds on an applied biosystems model 431 a peptide synthesizer using Fastmoc™ chemistry involving hbtu [2-(1h-benzotriazol-1-yl)-1.1.3.3-tetramethyluronium hexafluorophosphate, as published by Rao et al., Int. J. Pep. Prot. Res. 40:508–515 (1992). Peptides were cleaved following standard protocols and purified by reverse phase chromatography using standard methods. The amino acid sequence of each peptide was confirmed by automated Edman degradation on an Applied Biosystems 477 a protein sequencer/120a pth analyzer. More preferably, however, the compounds of this invention are synthesized in vivo by bacterial or plant cells which have been transformed by insertion of an expression cassette containing a synthetic gene which when transcribed and translated yields the desired compound. Such empty expression cassettes, providing appropriate regulatory sequences for plant or bacterial expression of the desired sequence, are also well-known, and the nucleotide sequence for the synthetic gene, either RNA or DNA, can readily be derived from the amino acid sequence for the protein using standard reference texts. Preferably, such synthetic genes will employ plant-preferred codons to enhance expression of the desired protein.

Industrial Applicability

The following description further exemplifies the compositions of this invention and the methods of making and using them. However, it will be understood that other methods, known by those of ordinary skill in the art to be equivalent, can also be employed.

Plants

The polypeptides employed in this invention can be effectively applied to plants afflicted with susceptible microorganisms by any convenient means, including spray, creams, dust or other formulation common to the antimicrobial arts. The compound can also be incorporated systemically into the tissues of a treated plant so that in the course of infesting the plant the pathogens will be exposed to antimicrobial amounts of the compound of this invention. One method of doing this is to incorporate the compound in a non-phytotoxic vehicle which is adapted for systemic administration to the susceptible plants. This method is commonly employed with fungicidal materials such as captan and is well within the purview of one of ordinary skill in the art of plant fungicide formulation. However, since the genes which code for these compounds can be inserted into an appropriate expression cassette and introduced into cells of a susceptible plant species, an especially preferred embodiment of this method involves inserting into the genome of the plant a DNA sequence coding for a compound of this invention in proper reading frame, together with transcription initiator and promoter sequences active in the plant. Transcription and translation of the DNA sequence under control of the regulatory sequences causes expression of the protein sequence at levels which provide an antimicrobial amount of the protein in the tissues of the plant which are normally infected by the pathogens. The plant is preferably a plant susceptible to infection and damage by one or more Fusarium graminearum, Fusarium moniliforme, Aspergillus flavus, Alternaria longipes, Sclerotinia sclerotiorum, and Sclerotinia trifoliorum. These include corn (Zea mays) and sorghum (Sorghum bicolor). However, this is not to be construed as limiting, inasmuch as these two species are among the most difficult commercial crops to reliably transform and regenerate, and these pathogens also infect certain other crops. Thus the methods of this invention are readily applicable via conventional techniques to numerous plant species, if they are found to be susceptible to the plant pathogens listed hereinabove, including, without limitation, species from the genera Allium, Antirrhinum, Arabidopsis, Arachis, Asparagus, Atropa, Avena, Beta, Brassica, Browallia, Capsicum, Cicer, Cicla, Citrullus, Citrus, Cucumis, Cucurbita, Datura Daucus, Digitalis, Fagopyrum, Fragaria, Geranium, Glycine, Gossypium, Helianthus, Hordeum, Hemerocallis, Lactuca, Lens, Lolium, Lotus, Lycopersicon, Majorana, Manihot, Medicago, Nasturtium, Nicotiana, Oryza, Pelargonium, Persea, Petunia, Phaseolus, Pisum, Ranunculus, Raphanus, Ricinus, Saccharum, Secale, Senecio, Setaria, Solanum, Spinacia, Trifolium, Triticum, Cromus, Cichorium, Hyoscyamus, Linum, Nemesia, Panicum, Onobrychis, Pennisetum, Salpiglossis, Sinapis, Trigonella, and Vigna.

Preferred plants that are to be transformed according to the methods of this invention are cereal crops, including maize, rye, barley, wheat, sorghum, oats, millet, rice, triticale, sunflower, alfalfa, rapeseed and soybean.

Synthetic dna sequence can then be prepared which code for the appropriate sequence of amino acids, and this synthetic dna sequence can be inserted into an appropriate plant expression cassette.

Likewise, numerous plant expression cassettes and vectors are well known in the art. By the term "expression cassette" is meant a complete set of control sequences including initiation, promoter and termination sequences which function in a plant cell when they flank a structural gene in the proper reading frame. Expression cassettes frequently and preferably contain an assortment of restriction sites suitable for cleavage and insertion of any desired structural gene. It is important that the cloned gene have a start codon in the correct reading frame for the structural sequence. In addition, the plant expression cassette preferably includes a strong constitutive promoter sequence at one end to cause the gene to be transcribed at a high frequency, and a poly-a recognition sequence at the other end for proper processing and transport of the messenger RNA. An example of such a preferred (empty) expression cassette into which the cDNA of the present invention can be inserted is the pPHI414 plasmid developed by Beach et al. of Pioneer Hi-Bred International, Inc., Johnston, Id., as disclosed in U.S. patent application Ser. No. 07/785,648, filed Oct. 31, 1991. Highly preferred plant expression cassettes will be designed to include one or more selectable marker genes, such as kanamycin resistance or herbicide tolerance genes.

By the term "vector" herein is meant a DNA sequence which is able to replicate and express a foreign gene in a host cell. Typically, the vector has one or more endonuclease recognition sites which may be cut in a predictable fashion by use of the appropriate enzyme. Such vectors are preferably constructed to include additional structural gene sequences imparting antibiotic or herbicide resistance, which then serve as markers to identify and separate transformed cells. Preferred markers/selection agents include kanamycin, chlorosulfuron, phosphonothricin, hygromycin and methotrexate. A cell in which the foreign genetic material in a vector is functionally expressed has been "transformed" by the vector and is referred to as a "transformant."

A particularly preferred vector is a plasmid, by which is meant a circular double-stranded DNA molecule which is not a part of the chromosomes of the cell.

As mentioned above, both genomic and cDNA encoding the gene of interest may be used in this invention. The vector of interest may also be constructed partially from a cDNA clone and partially from a genomic clone. When the gene of interest has been isolated, genetic constructs are made which contain the necessary regulatory sequences to provide for efficient expression of the gene in the host cell. According to this invention, the genetic construct will contain (a) a first genetic sequence coding for the protein or trait of interest and (b) one or more regulatory sequences operably linked on either side of the structural gene of interest. Typically, the regulatory sequences will be selected from the group comprising of promoters and terminators. The regulatory sequences may be from autologous or heterologous sources.

Promoters that may be used in the genetic sequence include nos, ocs and camv promoters.

An efficient plant promoter that may be used is an overproducing plant promoter. Overproducing plant promoters that may be used in this invention include the promoter of the small sub-unit (ss) of the ribulose-1.5-biphosphate carboxylase from soybean (Berry-Lowe et al., J. Molecular and App. Gen., 1:483–498 (1982)), and the promoter of the cholorophyll a-b binding protein. These two promoters are known to be light-induced, in eukaryotic plant cells (see, for example, Genetic Engineering of Plants, An Agricultural Perspective, A. Cashmore, Pelham, N.Y., 1983, pp. 29–38, G. Coruzzi et al., J. Biol. Chem., 258:1399 (1983), and P. Dunsmuir, et al., J. Molecular and App. Gen., 2:285 (1983)).

The expression cassette comprising the structural gene for the protein of this invention operably linked to the desired control sequences can be ligated into a suitable cloning vector. In general, plasmid or viral (bacteriophage) vectors containing replication and control sequences derived from species compatible with the host cell are used. The cloning vector will typically carry a replication origin, as well as specific genes that are capable of providing phenotypic selection markers in transformed host cells. Typically, genes conferring resistance to antibiotics or selected herbicides are used. After the genetic material is introduced into the target cells, successfully transformed cells and/or colonies of cells can be isolated by selection on the basis of these markers.

Typically, an intermediate host cell will be used in the practice of this invention to increase the copy number of the cloning vector. With an increased copy number, the vector containing the gene of interest can be isolated in significant quantities for introduction into the desired plant cells. Host cells that can be used in the practice of this invention include prokaryotes, including bacterial hosts such as E. coli, S. typhimurium, and Serratia marcescens. Eukaryotic hosts such as yeast or filamentous fungi may also be used in this invention. Since these hosts are also microorganisms, it will be essential to ensure that plant promoters which do not cause expression of the protein in bacteria are used in the vector.

The isolated cloning vector will then be introduced into the plant cell using any convenient technique, including electroporation (in protoplasts), retroviruses, bombardment, and microinjection into cells from momocotyledonous or dicotyledonous plants in cell or tissue culture to provide transformed plant cells containing as foreign dna at least one copy of the DNA sequence of the plant expression cassette. Preferably, the monocotyledonous species will be selected from maize, sorghum, wheat or rice, and the dicotyledonous species will be selected from soybean, alfalfa, rapeseed, sunflower or tomato. Using known techniques, protoplasts can be regenerated and cell or tissue culture can be regenerated to form whole fertile plants which carry and express the gene for a protein according to this invention. Accordingly, a highly preferred embodiment of the present invention is a transformed maize plant, the cells of which contain as foreign dna at least one copy of the DNA sequence of an expression cassette of this invention.

Finally, this invention provides methods of imparting resistance to diseases caused by microorganisms selected from Fusarium graminearum, Fusarium moniliforme, Diplodia maydis, Colletototrichum graminicola, Verticillium alboatrum, Phytophthora megaspermae f.sp. glycinea, Macrophomina phaseolina, Diaporthe phaseolorum caulivora, Sclerotinia sclerotiorum, Sclerotinia trifoliorum, Aspergillus flavus to plants of a susceptible taxon, comprising the steps of:

a) culturing cells or tissues from at least one plant from the taxon, b) introducing into the cells or tissue culture at least one copy of an expression cassette comprising a structural gene for one or more of the compounds of this invention, operably linked to plant regulatory sequences which cause the expression of the compound or compounds in the cells, and c) regenerating disease-resistant whole plants from the cell or tissue culture. Once whole plants have been obtained, they can be sexually or clonally reproduced in such manner that at least one copy of the sequence provided by the expression cassette is present in the cells of progeny of the reproduction.

Alternatively, once a single transformed plant has been obtained by the foregoing recombinant DNA method, conventional plant breeding methods can be used to transfer the structural gene for the compound of this invention and associated regulatory sequences via crossing and backcrossing. Such intermediate methods will comprise the further steps of:

a) sexually crossing the disease-resistant plant with a plant from the disease-susceptible taxon;

b) recovering reproductive material from the progeny of the cross; and c) growing disease-resistant plants from the reproductive material. Where desirable or necessary, the agronomic characteristics of the susceptible taxon can be substantially preserved by expanding this method to include the further steps of repetitively:

a) backcrossing the disease-resistant progeny with disease-susceptible plants from the susceptible taxon; and b) selecting for expression of antimicrobial activity (or an associated marker gene) among the progeny of the backcross, until the desired percentage of the characteristics of the susceptible taxon are present in the progeny along with the gene imparting antimicrobial activity.

By the term "taxon" herein is meant a unit of botanical classification of genus or lower. It thus includes genus, species, cultivars, varieties, variants, and other minor taxonomic groups which lack a consistent nomenclature.

It will also be appreciated by those of ordinary skill that the plant vectors provided herein can be incorporated into Agrobacterium tumefaciens, which can then be used to transfer the vector into susceptible plant cells, primarily from dicotyledonous species. Thus, this invention provides a method for imparting antimicrobial activity and disease resistance in Agrobacterium tumefaciens—susceptible dicotyledonous plants in which the expression cassette is introduced into the cells by infecting the cells with Agrobacterium tumefaciens, a plasmid of which has been modified to include a plant expression cassette of this invention.

Human and Veterinary Pharmaceutical Use

This invention also provides methods of treating and preventing infection by susceptible organisms in a human or lower animal host in need of such treatment, which method comprises administration to the human or lower animal host in need of such treatment a therapeutically effective amount of a polypeptide of this invention or a composition containing one or more of the polypeptides. The polypeptides of the present invention may be administered parenterally, by inhalation spray, rectally or topically in dosage unit formulations containing conventional nontoxic pharmaceutically acceptable carriers, adjuvants and vehicles as desired. The term parenteral as used herein includes subcutaneous, intravenous, intramuscular, intraarticular and intrathecal injection and infusion techniques. As with other polypeptides, the polypeptides of this invention are not known to be active orally.

Total daily dose of the compounds of this invention administered to a host in single or divided doses may be in amounts, for example, of from 1 to 2000 mg/kg body weight daily and more usually 50 to 500 mg/kg. Dosage unit compositions may contain such amounts or fractions or submultiples thereof as appropriate to make up the daily dose. It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

This invention also provides pharmaceutical compositions in unit dosage form, comprising an effective amount of a compound of this invention in combination with a conventional pharmaceutical carrier. As used herein, the term "pharmaceutical carrier" means a solid or liquid filler, diluent or encapsulating material. Some examples of the materials which can serve as pharmaceutical carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such peanut oil, cottonseed oil, safflower oil, sesame oil, olive oil, corn oil and soybean oil; polyols such as propylene glycol, glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution, ethyl alcohol and phosphate buffer solutions, as well as other non-toxic compatible substances used in pharmaceutical formulations. Wetting agents, emulsifiers and lubricants such as sodium lauryl sulfate and magnesium stearate, as well as coloring agents, release agents, coating agents, and perfuming agents and preservatives can also be present in the compositions, according to the desires of the formulator. The amount of active ingredient that may be combined with the carrier materials to produce a single dosage form will vary depending upon the host treated and the particular mode of administration.

By "therapeutically effective amount" herein is meant an amount of either polypeptide or combination thereof sufficient to provide antimicrobial activity so as to alleviate or prevent infection by susceptible organisms in the human or lower animal being treated at a reasonable benefit/risk ratio attendant with any medical treatment.

Antifungal Testing

The antifungal activity of compounds synthesized in accord with this invention was measured using art-recognized methods, as described in Duvick et al., J. Biol. Chem. 26:18814–18820 (1992) against Aspergillus flavus, S. sclerotiorum, Fusarium graminearum and F. moniliforme. Results are shown in FIGS. 1 through 4.

In FIG. 1, the curves are labeled according to their SEQUENCE I.D. Nos., with the exception of the curve labeled "10," which reflects the performance of a crude mixture of correctly and incorrectly folded compounds, including some quantity of the compound having SEQUENCE I.D. No. 2. The two curves labeled "1" and "1a" represent results obtained with natural and synthetic hordothionin, respectively, both having the sequence shown in SEQUENCE I.D. No. 1.

Figure 2:
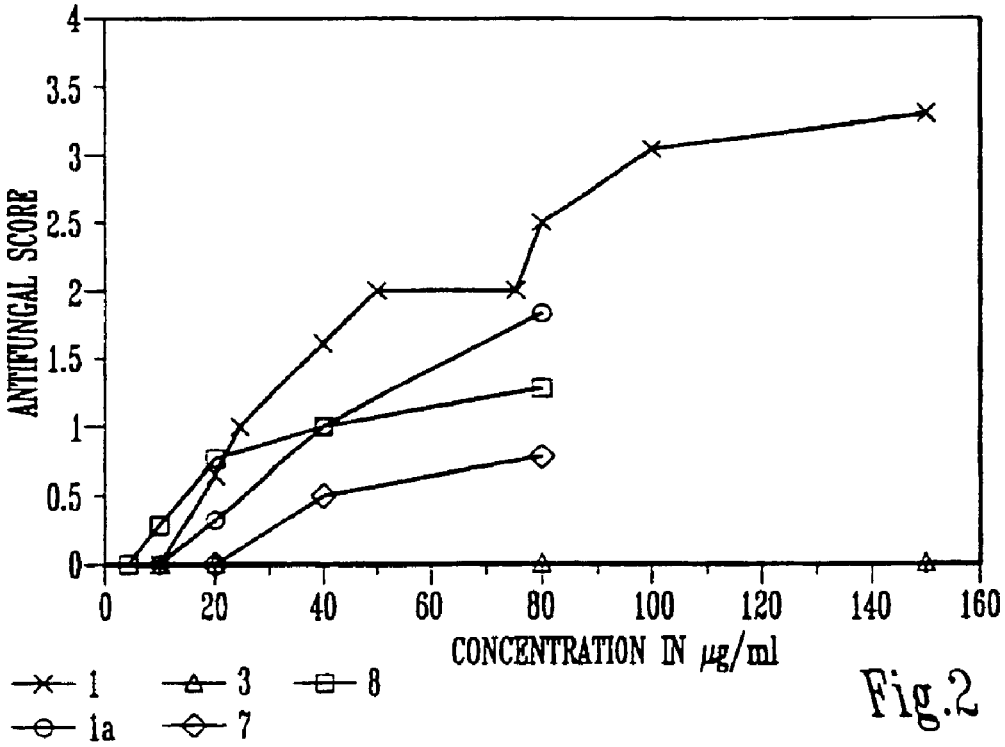
FIG. 2 is a graph of antimicrobial performance of various compounds discussed herein against A. flavus.
Figure 3:
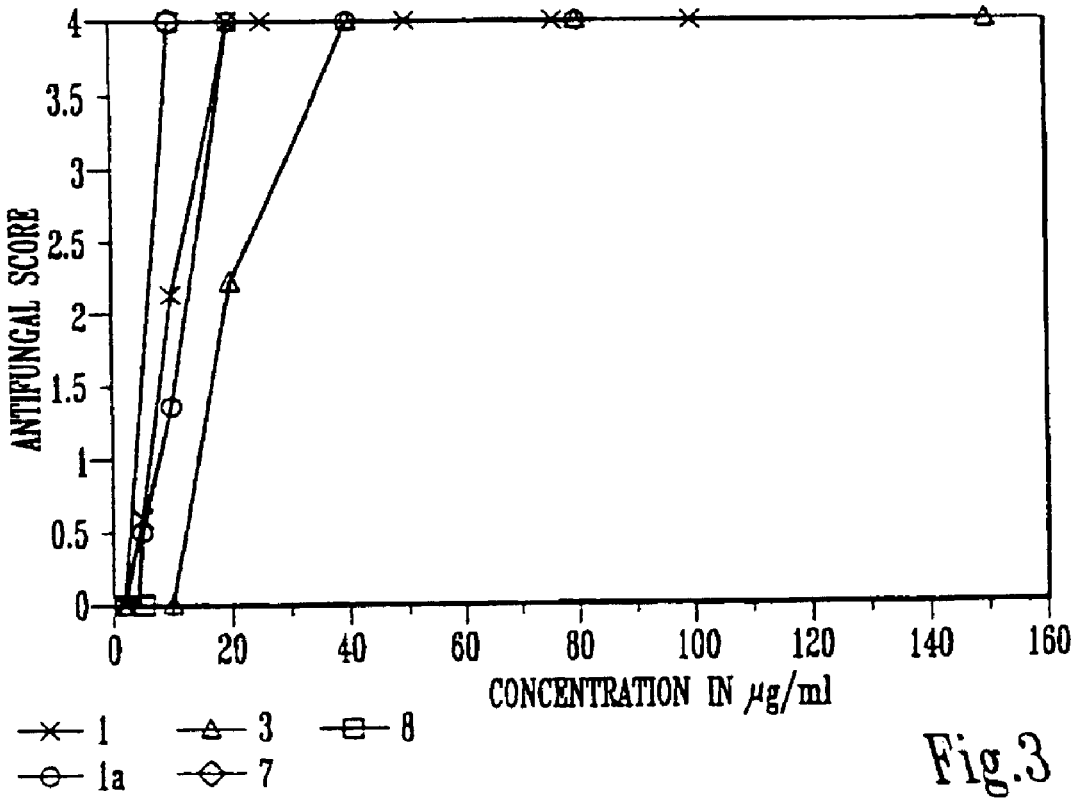
FIG. 3 is a graph of antimicrobial performance of various compounds discussed herein against F. graminearum.
Figure 4:
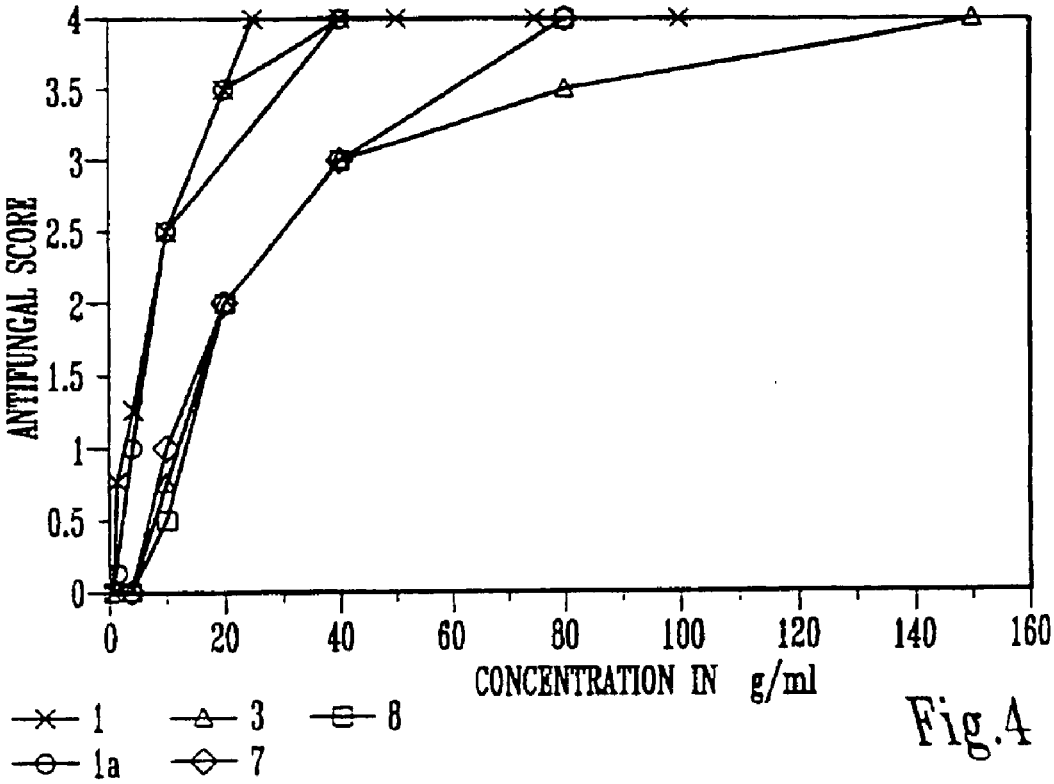
FIG. 4 is a graph of antimicrobial performance of various compounds discussed herein against F. moniliforme.

In FIGS. 2 through 4, the curves labeled as "1" and "1a" again represent results obtained with natural and synthetic hordonthionin, respectively, both having the sequence shown in SEQUENCE I.D. No. 1. The curves for other derivatives are labeled according to the SEQUENCE I.D. No. of the derivative.

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
(A) LENGTH: 45 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:1:

```
Lys Ser Cys Cys Arg Ser Thr Leu Gly Arg Asn Cys Tyr Asn Leu Cys
 1               5                  10                  15

Arg Val Arg Gly Ala Gln Lys Leu Cys Ala Gly Val Cys Arg Cys Lys
            20                  25                  30

Leu Thr Ser Ser Gly Lys Cys Pro Thr Gly Phe Pro Lys
        35                  40                  45
```

What is claimed is:

1. A protein having the sequence of SEQUENCE [1] *I.D.* No. 1 wherein the amino acid residues at one or more of positions 5, [10,] 11, [12,] 17, 19, 22, 30 and 41 are lysine, and the remainder of the residues at those positions are the residues at the corresponding positions in SEQUENCE I.D. No. 1.

2. A protein according to claim 1, wherein one or more of the amino acid residues at positions 5, 11, [12,] 17, 19, 22 and 41 are lysine.

3. A protein according to claim 2, wherein all of the amino acid residues at positions 5, 11, 12, 17, 19, 22 and 41 are lysine.

4. A nucleotide sequence which codes for [a] *the* protein according to claim 1.

5. An RNA sequence [according to claim 4] *that encodes the protein of claim 1*.

6. A DNA sequence [according to claim 4] *that encodes the protein of claim 1*.

7. An expression cassette containing the DNA sequence of claim 6 operably linked to plant regulatory sequences which cause the expression of the DNA sequence in plant cells.

8. A bacterial transformation vector comprising [an] *the* expression cassette according to claim 7[.] operably linked to bacterial expression regulatory sequences which cause replication of the expression cassette in bacterial cells.

9. Bacterial cells containing as a foreign plasmid at least one copy of [a] *the* bacterial transformation vector according to claim 8.

10. Transformed plant cells containing at least one copy of the expression cassette of claim 7.

11. [Transformed] *The transformed* cells according to claim 10, further characterized in being cells of a monocotyledonous species.

12. [Transformed] *The transformed* cells according to claim 11, further characterized in being maize, sorghum, wheat or rice cells.

13. [Transformed] *The transformed* cells according to claim 10, further characterized in being cells of a dicotyledonous species.

14. [Transformed] *The transformed* cells according to claim 13, further characterized in being soybean, alfalfa, rapeseed, sunflower, tobacco or tomato cells.

15. [A maize cell or tissue culture comprising] *The transformed* cells [according to claim 12] *of claim 11 wherein the cells are maize cells*.

16. A transformed plant comprising transformed cells according to claim 10.

17. A method for killing and inhibiting plant pathogenic microorganisms which are susceptible to [a]α-Hordothionin [comprising], *wherein the method comprises* introducing into the environment of the pathogenic microorganisms an antimicrobial amount of [a] *the* protein according to claim 1.

18. A method for killing and inhibiting plant pathogens selected from Fusarium graminearum, Fusarium moniliforme, Diplodia maydis, Colletototrichum graminicola, Verticillum alboatrum, Phytophthora megaspermae f.sp. glycinea, Macrophomina phaseolina, Diaporthe phaseolorum caulivora, Sclerotinia sclerotiorum, Sclerotinia trifoliorum, and Aspergillus flavus, [comprising] *wherein the method comprises* introducing into the environment of the pathogenic microorganisms an antimicrobial amount of [a] *the* protein according to claim 1.

19. A method according to claim 17, wherein the environment of the pathogen is the tissues of a living plant.

20. A method for enhancing the lysine content of a plant cell or seed [comprising the step of causing a], *wherein the method comprises transforming a plant cell by insertion of the expression cassette of claim 7 such that the* protein [according to claim 1 to be] *is* expressed in the cell or seed.

21. A method for enhancing the lysine content of a plant [comprising the step of causing a], *wherein the method comprises transforming a plant cell by insertion of the expression cassette of claim 7 such that the* protein [according to claim 1 to be] *is* expressed in tissues of the plant.

* * * * *

UNITED STATES PATENT AND TRADEMARK OFFICE

CERTIFICATE OF CORRECTION

PATENT NO. : RE 39,562 E
APPLICATION NO. : 10/010709
DATED : April 10, 2007
INVENTOR(S) : Rao et al.

It is certified that error appears in the above-identified patent and that said Letters Patent is hereby corrected as shown below:

Column 10
Lines 43-52 should read as follows:
--18. A method for killing and inhibiting plant pathogens selected from *the group consisting of*: Fusarium graminearum, Fusarium moniliforme, Diplodia maydis, Colletototrichum graminicola, Verticillum alboatrum Phytophthora megaspermae f.sp. glycinea, Macrophomina phaseolina, Diaporthe phaseolorum caulivora, Sclerotinia sclerotiorum, Sclerotinia trifoliorum, and Aspergillus flavus, [comprising] *wherein the method comprises* introducing into the environment of the pathogenic microorganisms an antimicrobial amount of [a] *the* protein according to claim 1--

Signed and Sealed this

Twelfth Day of June, 2007

JON W. DUDAS
*Director of the United States Patent and Trademark Office*